United States Patent [19]

Keyworth

[11] Patent Number: 4,571,439

[45] Date of Patent: Feb. 18, 1986

[54] METHOD FOR CONTROLLED OLIGOMERIZATION/ETHERIFICATION OF PROPYLENE

[75] Inventor: Donald A. Keyworth, Houston, Tex.

[73] Assignee: Tenneco Oil Company, Houston, Tex.

[21] Appl. No.: 757,483

[22] Filed: Jul. 22, 1985

[51] Int. Cl.$^4$ .................. C07C 43/04; C07C 2/28
[52] U.S. Cl. .................. 568/697; 585/510;
585/515; 585/520; 585/526
[58] Field of Search .......... 568/697; 585/510, 515,
585/520, 521, 526

[56] References Cited

U.S. PATENT DOCUMENTS

| | | | |
|---|---|---|---|
| 2,870,217 | 1/1959 | Toland | 568/697 |
| 3,979,461 | 9/1976 | Ancillotti et al. | 568/697 |
| 4,039,590 | 8/1977 | Ancillotti et al. | 568/697 |
| 4,242,530 | 12/1980 | Smith, Jr. | 585/510 |
| 4,262,146 | 4/1981 | Childs | 568/697 |
| 4,270,929 | 6/1981 | Dang Vu et al. | 585/14 |
| 4,282,389 | 8/1981 | Droste et al. | 568/697 |
| 4,301,315 | 11/1981 | Haskell et al. | 585/304 |
| 4,313,016 | 1/1982 | Manning | 585/832 |
| 4,320,233 | 3/1982 | Makovec et al. | 585/697 |
| 4,375,576 | 3/1983 | Smith, Jr. | 585/510 |
| 4,377,393 | 3/1983 | Schleppinghoff | 568/697 |
| 4,400,565 | 8/1983 | Darden et al. | 585/10 |
| 4,463,211 | 7/1984 | Manning | 585/510 |
| 4,482,775 | 11/1984 | Smith, Jr. | 585/671 |

FOREIGN PATENT DOCUMENTS 214604  3/1983  Fed. Rep. of Germany ...... 585/510

*Primary Examiner*—John Doll
*Assistant Examiner*—A. Pal
*Attorney, Agent, or Firm*—Kenneth H. Johnson

[57] ABSTRACT

Propylene contained in mixed $C_3/C_4$ streams containing at least 5 wt. % isobutene, for example, catalytic cracker offgas, may be recovered as a useful gasoline component by reacting in the presence of methanol to etherify and oligomerize the propylene in liquid phase at 80° to 130° C. at LHSV 2 to 5 in the presence of an acidic cation exchange resin whereby the product contains oligomers which are primary $C_6$ to $C_8$ mono olefins, methyl isopropyl ether, methyl tertiary butyl ether and unreacted material, by maintaining a residual of methanol in the product stream of 0.03 to 0.9 wt. % based on the product stream.

15 Claims, No Drawings

METHOD FOR CONTROLLED OLIGOMERIZATION/ETHERIFICATION OF PROPYLENE

BACKGROUND OF THE INVENTION

1. Field of the Invention

The present invention relates to etherification and/or oligomerization, particularly dimerization, of propylene in streams containing $C_3$ and $C_4$ alkenes using acid cation exchange resin catalyst in the presence of methanol.

2. Related Art

Refinery streams such as catalytic cracker offgas often contain large quantities of propylene in a mixture with various $C_4$'s (n-butene, isobutene, n-butane and isobutane). There has been a great deal of research directed to recovering the $C_4$'s e.g., by etherification, fractionation and oligomerization using acid cation exchange resins, however, the $C_3$'s which include propylene have generally been treated as inerts in these processes, in the same manner as isobutane and n-butane.

The reaction of olefins, including propylene to produce long chain polymers, using certain organo-metallic catalysts is well known. The best known catalysts are homogeneous catalysts consisting of compounds of metals of groups II to VI of the Periodic Table of Elements in combination with other compounds of metals of groups I to III, such as the Ziegler catalysts, which are preferably specific combinations of titanium halide and trialkyl aluminum component with or without other metal promoters. Alkyl aluminum halides in combination alkyl titanium esters are another example of a homogeneous catalyst used for this reaction. Low molecular weight polymers, i.e., dimers and trimers have been produced by using extremely low concentrations of these catalysts.

Similarly, free radial carbonium and carbanions have also been used to promote alpha-olefin polymerization and acid cation exchange resins have been used extensively for oligomerization, for example, U.S. Pat. Nos. 4,100,220; 4,215,011; 4,242,530; 4,232,177; 4,375,576; 4,463,211 and UK Patent Specifications 973,555 and 2,086,415B.

Other acid catalyst for oligomerizations include sulfuric acid (U.S. Pat. Nos. 3,546,317 and 3,832,418) and perfluorosulfonic acid resin (U.S. Pat. No. 4,065,512), phosphoric acid (Ipatieff, V. N., "Catalytic Polymerization of Gaseous Olefins by Liquid Phosphoric Acid", Ing and Eng, Ch. 27, No. 9 [1935] p. 1067-1071). In the vapor phase Ipatieff observed that phosphoric acid polymerization of propylene was accelerated by the presence of butene-1 or by polymerizing butene-1 prior to propylene. The product comprises primarily $C_9$ and higher polymers. It was also found that butene-2 and isobutene had the same effect.

The etherification of propylene is not widely discussed in the art, and in fact it is not easily obtained in significant yields with acid catalysts, particularly the cation exchange resins. However, methyl isopropyl ether (MIPE) can be expected to be a desirable octane improver.

In the present invention it has been found that the reactions of propylene, namely etherification and/or oligomerization can be improved and controlled by having specified amounts of isobutene and methanol present during the reaction.

It is an advantage of the present invention that a liquid phase reaction may be carried out to etherify and/or oligomerize propylene in improved conversion from low value mixed $C_3$–$C_4$ streams. It is a further advantage that a method is provided for the etherification of propylene with methanol in this low value stream, since methyl isopropyl ether will act as a gasoline octane improver. It is a particular advantage that a mixed product of oligomers, principally dimers and codimers of propylene and isobutene and methyl ethers of propylene and isobutene which comprises a valuable gasoline or blending stock may be obtained. It is a special feature of the present invention the oligomers produced are principally dimers which have higher octane numbers for gasoline blending than higher oligomers. It is an additional advantage that the presence of methanol in the reaction in the proper amount exerts a leveling effect on the catalyst such that the exothermic reaction proceeds at moderate temperatures without hot spots or polymer fouling in the catalyst bed.

SUMMARY OF THE INVENTION

The present invention is a process for the reaction of propylene in a hydrocarbon feed stream containing at least 5 weight % isobutene based on said feed stream in liquid phase with an acidic cation exchange resin at temperatures in the range of 80°–130° C., preferably 90 to 120° C. at LHSV in the range of 2 to 5 in the presence methanol to produce a product stream essentially comprising $C_6$ to $C_8$ monoolefins, methyl isobutyl ether and unreacted material, the amount of said methanol present being determined by a residual of said methanol in said product stream in the range of 0.03 to 0.9 wt. %, preferably about 0.1 to about 0.8 wt. %, based on the product stream.

The essential features of the present invention are (1) the presence of the isobutene and (2) the control of the methanol residual in the product stream in the ranges specified. The amount of residual methanol can be controlled by several variables, namely the amount of methanol fed to the reaction, the temperature of the reaction (which will effect conversion) and the feed rate and amount of isobutene and propylene in the feed. The control is maintained by constant monitoring of feed rates of methanol, feed rates and constitution of hydrocarbon feed streams, temperature of feed, reaction and heat exchange medium and methanol content of the product stream. For example, if the methanol residual drops, an increase methanol feed rate or reduction of the heat of reaction will increase the residual methanol.

A further feature of the present invention the control over product distribution obtained by maintaining the methanol residual in specific portions of the recited range. In the methanol residual range of 0.03 to 0.3 wt. % the principal reaction products are $C_6$ to $C_8$ monoolefins and methyl isopropyl ether and unreacted materials with methyl tertiary butyl ether being present. As the residual methanol increases in the specified range the selectivity to MTBE increases. With methanol residual in the range of 0.5 to 0.9 wt. % the product shifts such that the principal products of propylene and isobutene are their respective ethers, i.e., MIPE (some small amounts of methyl normal propyl ether are produced) and MTBE (some methyl secondary butyl ether) and oligomer and principally $C_8$ monoolefins from n-butenes. In other words, the product distribution shifts from oligomer in the presence of the lower concentrations of residual methanol to ethers in the higher concentrations of residual methanol.

In methanol etherifications of isobutene in $C_4$ streams, for the purpose of producing methyl tertiary butyl ether (MTBE) in fixed bed liquid phase, single pass procedures there is normally an excess of methanol present to suppress oligomer formation and to form as much MTBE as possible. The residual methanol in these systems is generally 5 to 10 weight %. Generally the feeds in such processes are $C_4$ cuts which contain contain little $C_3$'s. In the present reaction it has been observed that high ratios of methanol to isobutene, i.e., those that produce residual methanol in the product stream in excess of 0.9 wt. %, that MTBE is the principal product and only minor amounts of oligomer and methyl isopropyl ether were formed. Hence, when larger excesses of methanol than 1% are present in the product stream isobutene/methanol etherification is the dominant reaction and the propylene ether is suppressed. When the methanol residual drops below 0.03 volume % the conversion of propylene drops substantially.

In the absence of isobutene the propylene is substantially unreactive. Isobutene is the most reactive component of a $C_3/C_4$ stream, and for streams containing more than 30 weight percent isobutene, it would usually be desirable to react such a stream with sufficient methanol to produce methyl tertiary butyl ether and avoid oligomerization since MTBE as a gasoline octane improver is more valuable. The oligomer portion of the product of the present invention however, is an excellent blending material for gasolines. Preferably $C_3/C_4$ streams employed in the present invention contain from about 8 to 15 weight % isobutene.

DETAILED DESCRIPTION OF THE INVENTION

Catalytic cracker offgas (feed to the alkylator) in some refineries is out of balance, producing too much offgas for proper alkylator operation. This is especially the case where heavier feedstocks lead to greater volumes of catalytic cracker offgas.

Typically light olefins in catalytic cracker offgas are contained in a mixture of propane, propylene, isobutane, isobutene and n-butenes in a weight ratio of 10:35:30:7:20. Butenes have competitive use as alkylation feedstock and direct blendings into gasoline to improve octane performance. Thus the entire stream may be used as a feed for the present process or since isobutene is the most volatile of butenes, a separation made to recover all of the $C_3$ and enriched in isobutene in the $C_3/C_4$ fraction. Generally the gas stream used in the present process is a mixed $C_3/C_4$ hydrocarbon stream which may contain 0 to 60 wt. % propane, 5 to 90 wt. % propylene, 0 to 60 wt. % isobutane, 0 to 60 wt. % n-butane, 0 to 60 wt. % n-butenes and 5 to 30 wt. % isobutene. Preferably the total $C_4$'s in the stream comprise only about 10 to 60 % of the stream with isobutene being present in the range of 8 to 15 wt. % and propylene comprising 10 to 80 wt. % of the stream.

In oligomerization/etherification according to the present invention, not only does the isobutene etherify to form MTBE and oligomerize substantially completely with the formation of octenes, but also branched heptenes are formed. Propylene in the absence of isobutene is quite unreactive and requires 900 psi pressure to maintain it in liquid phase at 100° C., at which temperature conversions are less than 3%. At higher temperatures higher pressures are required and conversions are still below 10%. The oligomer product is mainly nonenes, which were not high octane components, and are not of preferred volatility. However, in the presence of isobutene and methanol as described the conversion of propylene is much higher, i.e., 28–75% at lower temperatures and pressures, with the product being substantially entirely octenes, heptenes and hexenes, MIPE and MTBE which all have high octane numbers.

In the presence of isobutene, propylene conversions exceed 10% at lower pressures, and as noted above the oligomer is primarily $C_6$ to $C_8$ mono olefins. More specifically over 90 wt. %, i.e., substantially all of the oligomer product is less than $C_8$ with nonenes and higher olefins being negligible. N-butenes are not detrimental to the present process and are relatively unreactive at the preferred temperature of 90°–100° C. Further, isobutene is preferred because a cut can be made incorporating the isobutene with propylene, while leaving the n-butenes with the pentenes for alkylation feedstock.

The pressure of the present reaction system is not critical, however it must be sufficient to maintain the reactants in liquid phase during the reaction and as set out above, the presence of the isobutene (and other $C_4$'s) reduces the pressure required to maintain the liquid phase.

The catalysts useful for the present invention are preferably in the macroreticular form which has surface areas of from 20 to 600 square meters per gram. Catalysts suitable for the present process preferably are cation exchangers, which contain sulfonic acid groups, and which have been obtained by polymerization or copolymerization of aromatic vinyl compounds followed by sulfonation. Examples of aromatic vinyl compounds suitable for preparing polymers or copolymers are: styrene, vinyl toluene, vinyl naphthalene, vinyl ethylbenzene, methyl styrene, vinyl chlorobenzene and vinyl xylene. A variety of methods may be used for preparing these polymers; for example, polymerization alone or in admixture with other monovinyl compounds, or by crosslinking with polyvinyl compounds; for example, with divinyl benzenes, divinyl toluenes, divinylphenylethers and others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric acid or chlorosulfonic acid, or by copolymerizing aromatic compounds which contain sulfonic acid groups (see e.g., U.S. Pat. No. 2,366,007). Further sulfonic acid groups may be introduced into these polymers which already contain sulfonic acid groups; for example, by treatment with fuming sulfuric acid, i.e., sulfuric acid which contains sulfur trioxide. The treatment with fuming sulfuric acid is preferably carried out at 0° to 150° C., and the sulfuric acid should contain unreacted sulfur trioxide after the reaction. The resulting products preferably contain an average of 1.3 to 1.8 sulfonic acid groups per aromatic nucleus. Particularly, suitable polymers which contain sulfonic acid groups and are copolymers of aromatic monovinyl compounds with aromatic polyvinyl compounds, particularly divinyl compounds, in which the polyvinyl benzene content is preferably 1 to 20% by weight of the copolymer (see, for example, German Patent Specification 908,247).

Thermally stabilized acidic cation exchange resins may also be employed. Varying degrees of stabilization have been obtained by the incorporation of electron withdrawing groups, particularly halogens, such as bromine and chlorine into the resin polymer. U.S. Pat. Nos. 3,256,250; 3,342,755; 4,269,943 and British Pat. No. 1,393,594 describe several such procedures.

A preferred stabilized catalyst of this type is that described in U.S. Pat. No. 4,269,943, wherein chlorine or bromine are added to the polymer prior to sulfonation. In this manner the halogen is attached to the aromatic nuclei of the resin polymer. A particularly preferred form of this catalyst is the chlorine stabilized catalyst.

The thermal stability may also be obtained by attachment of $-SO_3H$ groups at the para position to the divinyl benzene and ethylstyrene units (the ethyl and/or vinyl groups being attached in the meta position relative to each other). This is discussed in an article by Leonardus Petrus, Elze J. Stamhuls and Geert E. J. Joosten, "Thermal Deactivation of Strong-Acid Ion-Exchange Resins in Water", Ind. Eng. Chem. Prod. Res. Dev. 1981, 20, pages 366-377.

The ion exchange resin is preferably used in a granular size of about 0.25 to 2 mm, although particles from 0.15 mm up to about 2 mm may be employed. The finer catalysts provide high surface area, but also result in high pressure drops through the reactor. The increased pressure drop as a result of the smaller granular size, may be offset by using shorter reactor tubes, i.e., from about 2 to 4 ft. long. However, catalyst particles of the preferred size and substantially free of fines are not subject to the large pressure drops. The preferred granular size is 15 to 40 mesh (approximately 0.420 to 1.3 mm), which is substantially free of fines. At the LHSV's of the present invention the preferred granular size can be used in longer tubes, i.e., six to seven feet without excessive pressure drops, i.e., less than 50 psig.

The life of the catalyst can also be adversely affected by catalyst poisons. The feed to the reactor should be free of any poisons, which include cations, particularly metals, and amines.

The catalyst is employed in a fixed bed with a flow of hydrocarbon stream therethrough. The fixed bed may be in a single continuous bed with heat exchange means located therein or more preferable the reactor is a tubular reactor wherein a plurality of tubes of ⅛ to 2 inches outside diameter are mounted in a shell. The catalyst is loaded in the tubes and heat exchange medium at the desired temperatures passes through the shell and around the tubes.

Various feed compositions utilized in the present process have produced polymer gasoline (after debutanizing) of very good octane number for use in blending or as a gasoline stock per se, e.g., RON of 101.5 and MON of 82.8 and RVP of 1.7 psi.

The following examples are intended to illustrate the invention and not to limit its scope.

EXAMPLES

A charge (100 cc) of fresh methanol wetted acidic cation exchange resin (Rohm and Haas Amberlyst 252-H, macroreticular resin of sulfonated styrene divinyl benzene copolymer) was loaded into a ½ inch diameter jacketed and essentially isothermal reactor. The feed tank was pressured to 180 psig with nitrogen. Liquid feed was pumped with a Milton Roy mini-pump downflow through the catalyst bed. The reactor temperature was maintained by circulating heated silicone oil through the reactor's jacket. The pressure of the reaction was maintained by a back-pressure regulator.

The length of ½ inch tubing to contain 100 cc of catalyst is 636 cm. The reaction product was collected in a high pressure collector, and transferred through a septum cap into tared, capped weighing bottles chilled in a dry ice/acetone bath at $-90°$ C. containing ethyl benzene which reduces the vapor pressure of the propylene and prevents losses. The sample while cold ($-90°$ C.) is analyzed by gas chromatograph.

The runs in the TABLE were carried out over a three month period, usually for about seven hours a day, each represents the conditions and results after the reaction stabilized or of composite results taken several times during the run or the runs are arranged in order of increasing methanol residual in the product stream. The pressure in each run was 700 psig and the LHSV was about 3 for each run. The following abbreviations are used in the TABLE.

Ex—Example
Wt %—weight percent
$C_3^=$—propylene
MeOH—Methanol
$nB^=$—normal butenes
$IB^=$—isobutene
nB—n-butane
MOE—methyl ethers of propylene
MTBE—methyl tertiary butyl ether
MSBE—methyl secondary butyl ether
$C_{6+}$—oligomer of greater than 6 carbon atoms
Exo—exotherm (hot spot in catalyst bed)

| | FEED WEIGHT % | | | | | MeOH Residuals | PRODUCT CONVERSION WT. % | | | SELECTIVITY OLEFIN | | | WT. % | REACTOR TEMP °C. | |
|---|---|---|---|---|---|---|---|---|---|---|---|---|---|---|---|
| Ex | $C_3^=$ | MeOH | $nB^=$ | $IB^=$ | nB | Wt. % | $C_3^=$ | $nB^=$ | $IB^=$ | MOE | MTBE | MSBE | $C_{6+}$ | BATH | EXO |
| 1 | 28.9 | 0 | 20.5 | 12.1 | 38.5 | 0 | 25.1 | 13 | 100 | 0 | 0 | 0 | 15.1 | 96 | 108 |
| 2 | 26.8 | 5.7 | 18.7 | 12.5 | 36.3 | 0 | 34.4 | 6 | 97 | 72 | 0 | 100 | 13.1 | 96 | 115 |
| 3 | 27.3 | 5.7 | 19.3 | 11.4 | 36.2 | <0.1 | 44 | 23 | 78 | 55 | 10 | 28 | 13.4 | 95 | 113 |
| 4 | 24.5 | 6.8 | 18.9 | 18.0 | 32.2 | 0.03 | 55 | 54 | 94 | 85 | 3 | 26 | 30.5 | 105 | 127 |
| 5 | 21.6 | 6.5 | 19.3 | 6.7 | 39.3 | 0.11 | 55 | 61 | 100 | 55 | 4 | 10 | 14.4 | 105 | 118 |
| 6 | 26.2 | 6.5 | 20.6 | 7.6 | 37.5 | 0.3 | 51 | 8 | 75 | 28 | 80 | 27 | 8.2 | 106 | 115 |
| 7 | 26.2 | 6.5 | 20.6 | 7.6 | 37.5 | 0.7 | 39 | 21 | 63 | 37 | 86 | 31 | 5.0 | 95 | 116 |
| 8 | 21.6 | 6.5 | 19.4 | 6.7 | 39.3 | 0.9 | 28 | 10 | 74 | 59 | 78 | 70 | 5.1 | 95 | 115 |
| 9 | 26.9 | 6.8 | 19.1 | 11.3 | 35.9 | 0.9 | 10 | 18 | 80 | 100 | 100 | 16 | 1.6 | 85 | 100 |
| 10 | 26.9 | 6.8 | 19.1 | 11.3 | 35.9 | 1.0 | 3 | 8 | 95 | 100 | 77 | 17 | 0 | 85 | 100 |
| 11 | 26.9 | 6.8 | 19.1 | 11.3 | 35.9 | 1.3 | 10 | 7 | 90 | 100 | 67 | 37 | 1.7 | 96 | 112 |
| 12 | 26.9 | 6.8 | 19.1 | 11.3 | 35.9 | 1.5 | 4 | 13 | 85 | 100 | 78 | 13 | 0.1 | 90 | 107 |
| 13 | 21.0 | 9.6 | 20.0 | 7.4 | 36.2 | 2.9 | <10 | <10 | 92 | — | 100 | — | 0.4 | 95 | 112 |
| 14 | 24.0 | 16.2 | 18.9 | 6.9 | 35.4 | 8.9 | <10 | <10 | 93 | — | 96 | — | 0.8 | 95 | 109 |

The invention claimed is:

1. A process for the reaction of propylene in a hydrocarbon feed stream comprising contacting said feed stream containing propylene and at least 5 weight % isobutene based on said feed stream in liquid phase with an acidic cation exchange resin at temperatures in the range of 80°–130° C. at LHSV in the range of 2 to 5 in the presence of methanol to produce a product stream essentially comprising $C_6$ to $C_8$ mono olefins, methyl isopropyl ether, methyl tertiary butyl ether and unreacted material, the amount of methanol present being determined by a residual of said methanol in said product stream in the range of 0.03 to 0.9 wt. % based on said product stream.

2. The process according to claim 1 wherein up to 30 weight % isobutene is present in said feed stream.

3. The process according to claim 1 wherein from about 8 to 15 wt. % isobutene is present in said feed stream.

4. The process according to claim 1 wherein said feed stream is a $C_3/C_4$ hydrocarbon stream.

5. The process according to claim 4 wherein said feed stream contains propane, propylene, butane, n-butene, isobutane and isobutene.

6. The process according to claim 5 wherein said feed stream contains 0 to 60 wt. % propane, 5 to 90 wt. % propylene, 0 to 60 wt. % butane, 0 to 60 wt. % n-butenes, 0 to 60 wt. % isobutane and 5 to 30 wt. % isobutene.

7. The process according to claim 1 wherein the temperature is in the range of 90° to 120° C.

8. The process according to claim 1 wherein said feed stream contains from 5 to 90 wt. % propylene.

9. The process according to claim 1 wherein said oligomers in said product stream are comprised of over 90 wt. % $C_6$ to $C_8$ mono olefins.

10. The process according to claim 9 wherein said oligomers in said product stream are comprised of substantially all $C_6$ to $C_8$ mono olefins.

11. The process according to claim 1 wherein the amount of residual methanol present in said product stream is from 0.1 to 0.8 wt. % based on said product stream.

12. The process according to claim 1 wherein the amount of residual methanol present in said product stream is from 0.03 to 0.3 wt. % based on said product stream.

13. The process according to claim 1 wherein the amount of residual methanol present in said product stream is from 0.5 to 0.9 wt. % based on said product stream.

14. A process for the reaction of propylene in a $C_3/C_4$ hydrocarbon feed stream comprising contacting said feed stream containing from about 8 to 15 wt. % isobutene based on said feed stream in liquid phase with an acidic cation exchange resin at temperatures in the range of 90° to 120° C. at LHSV of 2 to 5 in the presence of methanol to produce a product stream containing oligomers, comprised of over 90 wt. % $C_6$ to $C_8$ mono olefins, methyl isopropyl ether, methyl tertiary butyl ether and unreacted material, the amount of methanol present being determined by a residual of said methanol in said product stream in the range of 0.03 to 0.8 wt. % based on said product stream.

15. The process according to claim 14 wherein said oligomers in said product stream are substantially all $C_6$ to $C_8$ mono olefins.

* * * * *